United States Patent [19]
Serlupi-Crescenzi et al.

[11] Patent Number: 6,004,813
[45] Date of Patent: Dec. 21, 1999

[54] IL-6 ACTIVITY INHIBITOR

[75] Inventors: Ottaviano Serlupi-Crescenzi; Annarita Pezzotti, both of Rome, Italy

[73] Assignee: Applied Research Systems ARS Holding N.V., Curacao, Netherlands Antilles

[21] Appl. No.: 08/945,726

[22] PCT Filed: May 11, 1995

[86] PCT No.: PCT/EP95/01778

§ 371 Date: Nov. 10, 1997

§ 102(e) Date: Nov. 10, 1997

[87] PCT Pub. No.: WO96/35782

PCT Pub. Date: Nov. 14, 1996

[51] Int. Cl.$^6$ ............................ C07H 21/04; C12N 15/11; C12N 15/85
[52] U.S. Cl. ............................ 435/375; 435/6; 435/320.1; 435/377; 435/455; 514/44; 536/23.1; 536/24.1; 536/24.5
[58] Field of Search ............................ 435/6, 320.1, 375, 435/377, 455; 536/24.1, 23.1, 24.5; 514/44

[56] References Cited

PUBLICATIONS

Stull et al. Antigene, Ribozyme and Aptamer Nucleic Acid Drugs: Progress and Prospects. Pharmaceutical Research vol. 12(4):465–483, 1995.
Agrawal, S. Antisense Oligonucelotides: Towards Clinical Trials. TIBTECH vol. 14:376–387, Oct. 1996.
S. Akira et al., "Molecular Cloning of APRF, a Novel IFN–Stimulated Gene Factor 3 p91–Related Transcription Factor Involved in the gp130–Mediated Signaling Pathway", Cell, vol. 77, pp. 63–71, Apr. 8, 1994.
A. Bielinska et al., "Regulation of Gene Expression With Double–Stranded Phosphorothioate Oligonucleotides", Science, vol. 250, p. 9971000, Nov. 16, 1990.
C. Clusel et al., "Ex Vivo Regulation of Specific Gene Expression by Nanomolar Concentration of Double–Stranded Dumbbell Oligonucleotides", Nucleic Acids Research, vol. 21, No. 15, pp. 3405–3411, Jun. 15, 1993.
W.S. Dynan et al., "The Promoter–Specific Transcription Factor Sp1 Binds to Upstream Sequences in the SV40 Early Promoter", Cell, vol. 35, pp. 79–87, Nov., 1983.
D.M. Fowlkes et al., "Potential Basis for Regulation of the Coordinately Expressed Fibrinogen Genes: Homology in the 5' Flanking Regions", Proc. Natl. Acad. Sci. USA, vol. 81, pp. 2313–2316, Apr., 1984.
L. Graeve et al., "Interleukin–6 In Autoimmune Diseases", Clinical Investigator, vol. 71, pp. 664–671, 1993.
P.C. Heinrich et al., "Interleukin–6 and the Acute Phase Response", Biochem. J., vol. 265, pp. 621–636, 1990.
G.M. Hocke et al., "Synergistic Action of Interleukin–6 and Glucocorticoids is Mediated by the Interleukin–6 Response Element of the Rat $\alpha_2$ Macroglobulin Gene"Molecular and Cellular Biology, vol. 12, No. 5, pp. 2282–2294, May, 1992.
Z.Y. Lu et al., "High Amounts of Circulating Interleukin (Il)–a6 in the Form of Monomeric Immune Complexes During Anti–Il–6 Therapy", Eur. J. Immunol., vol. 22, pp. 2819–2824, 1992.
B. Klein et al., "Murine Anti–Interleukin-6 Monoclonal Antibody Therapy for a Patient With Plasma Cell Leukemia", Blood, vol. 78, No. 5, pp. 1198–1204, Sep. 1, 1991.
D. Kunz et al., "Indentification of the Promoter Sequences Involved in the Interleukin–6 Dependent Expression of the Rat $\alpha_2$–Macroglobulin Gene", Nucleic Acids Research, vol. 17, No. 3, pp.1121–1139, 1989.
S. Oliviero et al., "The Human Haptoglobin Gene: Transcriptional Regulation During Development and Acute Phase Induction", The EMBO Journal, vol. 6, no. 7, pp. 1905–1912, 1987.
V. Poli et al., "Interleukin–6 Deficient Mice are Protected From Bone Loss Caused By Estrogen Depletion", The EMBO Journal, vol. 13, no. 5, pp. 1189–1196, 1994.
A. Ray et al., "On the Mechanism for Efficient Repression of the Interleukin–6 Promoter by Glucocorticoids: Enhancer, TATA Box, and RNA Start Site (Inr Motif) Occlusion", Molecular and Cellular Biology, vol. 10, No. 11, pp. 5736–5746, Nov., 1990.
K. Riabowol et al., "Transcription Factor AP–1 Activity is Required for Initiation of DNA Synthesis and is Lost During Cellular Aging", Proc. Natl. Acad. Sci. USA, vol. 89, pp. 157–161, Jan., 1992.
C. Toniatti et al., "Regulation of the Human C–Reactive Protein Gene, a Major Marker of Inflammation and Cancer", Mol. Biol. Med., vol. 7, pp. 199–212, 1990.
U.M. Wegenka et al., "Acute–Phase Response Factor, a Nuclear Factor Binding to Acute–Phase Response Elements Is Rapidly Activated by Interleukin–6 at the Posttranslational Level", Mol. Cel. and Biol., vol. 13, No. 1, pp. 276–288, Jan., 1993.
H. Wu et al., "Inhibition of In Vitro Transcription by Specific Double–Stranded Oligodeoxyribonucleotides", Gene, vol. 89, pp. 203–209, 1990.

(List continued on next page.)

*Primary Examiner*—Nancy Degen
*Assistant Examiner*—Sean McGarry
*Attorney, Agent, or Firm*—Browdy and Neimark

[57] ABSTRACT

The invention relates to a nucleotide sequence, which is able to inhibit the IL-6 activity, its use in therapy as well as pharmaceutical compositions containing it.

In particular, it relates to a nucleotide sequence which comprises:
i) at least one nucleotide sequence that is an APRE element of general formula ZXMYKGKAA, wherein Z represents T or G or can also be absent, X represents T or can also be absent, M represents C or A, Y represents C or T and K represents T or G,
in conjunction with
ii) at least one nucleotide sequence constituting a transcription factor binding site other than the APRE element, such as those present in promoter regions.

14 Claims, 8 Drawing Sheets

OTHER PUBLICATIONS

T. Yoneda et al., "Neutralizing Antibodies to Human Interleukin 6 Reverse Hypercalcemia Associated With a Human Squamous Carcinoma", Cancer Research, vol. 53, pp. 737–740, Feb. 15, 1993.

J. Yuan et al., "The Signalling Pathways of Interleukin–6 and Gamma Interferon Converge by the Activation of Different Transcription Factors Which Bind to Common Responsive DNA Elements", Mol. Cel. Biol., vol. 14, pp. 1657–1668, Mar., 1994.

M. Zenke et al., "Multiple Sequence Motifs are Involved in SV40 Enhancer Function", The EMBO Journal, vol. 5, No. 2, pp. 387–397, 1986.

O. Serlupi–Crescenzi et al., "Il–6 Response of Acute Phase Promoter Gene Fragments in HEPG2 Cells. Setting–up of a Luciferase Assay"; The $12^{th}$ European Immunology Meeting, Barcelona, Spain Jun. 14–17, 1994.

Figure 1    Construction of plasmid pM8SV

Figure 2   Sequence of the BamH I-Hind III inhibitor DNA fragment of plasmid M8SV

```
         BamHI\
CCCAGGATCC TTCTGGGAAT TCTGATCCTT CTGGGAATTC   40

TGATCCTTCT GGGAATTCTG ATCCTTCTGG GAATTCTGAT   80
      M8 sequence
CCTTCTGGGA ATTCTGATCC TTCTGGGAAT TCTGATCCTT  120
                                    /    \
CTGGGAATTC TGATCCTTCT GGGAATTCTG ATCTGCATCT  160

CAATTAGTCA GCAACCATAG TCCCGCCCCT AACTCCGCCC  200

ATCCCGCCCC TAACTCCGCC CAGTTCCGCC CATTCTCCGC  240
                    SV40 sequence
CCCATGGCTG ACTAATTTTT TTTATTTATG CAGAGGCCGA  280

GGCCGCCTCG GCCTCTGAGC TATTCCAGAA GTAGTGAGGA  320
                                           /
GGCTTTTTTG GAGGCCTAGG CTTTTGCAAA AAGCTT      356
                                        Hind III
```

Figure 3  IL-6 reporter gene assay in T47D and in M1 cells.
Test of different M8-containing plasmids Figure 4    Time course of luciferase inducibility by IL-6 in HepG2 cells Figure 5    HepG2 reporter gene assay for IL-6. Test of pM8 inhibitor plasmid against pM8SVL reporter gene plasmid Figure 6    HepG2 reporter gene assay for IL-6. Test of pM8SV inhibitor plasmid against pM8SVL reporter gene plasmid Figure 7   HepG2 reporter gene assay for IL-6. Test of pSV and pM8SV inhibitor plasmids against pM8SVL reporter gene plasmid Figure 8    HepG2 reporter gene assay for IL-6. Test of inhibitor plasmids against pHPSVL reporter gene plasmid

IL-6 ACTIVITY INHIBITOR

FIELD OF THE INVENTION

The present invention relates to a nucleotide sequence, which is able to inhibit the IL-6 activity, its use in therapy as well as pharmaceutical compositions containing it.

BACKGROUND OF THE INVENTION

IL-6 is a protein belonging to the group of cytokines, which proved to play a key role in the organism's immune response and haematopoiesis stimulation.

Many biological functions have, in fact, been found for IL-6 in the hematopoietic and lymphoid system, in the liver and in other target organs and cells. Some of these functions are beneficial, while others are related to pathological states. Among the latter functions, IL-6 has been found to be a growth factor for multiple myeloma cells; anti-IL-6 antibodies were shown to transiently block myeloma cell proliferation in a leukemic patient (see for example Klein et al., Blood, 78, (5), pp.1198–1204, 1991 and Lu et al., Eur. J. Immunol., 22, pp. 2819–24, 1992).

Elevated IL-6 levels have been correlated with autoimmune and inflammatory diseases, such as rheumatoid arthritis, glomerulonephritis, psoriasis, and Castelman's disease (see for example Graeve et al., Clin. Investig., 71, pp.664–71, 1993). IL-6 has also been shown to play a direct role in bone loss and hypercalcemia (see for example Poli et al., Embo J., 13, (5) pp. 1189–96 and Yoneda et al., Cancer Res., 53, pp. 737–40, February 1993).

The development of inhibitors of IL-6 activity has therefore been the subject of active research. For this purpose, different approaches have been pursued, including the use of antibodies against IL-6 (as reported by Klein et al. above), gp130 or gp80; the use of soluble gp130; or the use of muteins for IL-6, or IL-6 Receptor.

Since these approaches might be associated with specific unwanted effects in clinical applications (as reported by Lu et al., above), the setting-up of additional strategies to inhibit IL-6 activity would be useful.

The Applicant has, therefore, investigated a different approach to inhibit IL-6 activity: by blocking the intracellular proteins mediating the IL-6 signal.

The transduction of the IL-6 signal in responsive cells has been intensively investigated. Fowlkes et al. (PNAS USA, 81, pp. 2313–6, 1984) first suspected DNA responsive elements specific for IL-6 flanking the rat fibrinogen genes.

Later on, Kunz et al. (Nuc. Ac. Res., 17, (3), 1121–37, 1989) showed a responsive element with a core sequence identical to that of rat fibrinogen genes (CTGGGA) to respond to IL-6 in the rat $\alpha_2$-macroglobulin gene.

DNA responsive elements with sequences related to those above-mentioned have also been defined in the genes coding for the human C Reactive Protein (CRP) (see Toniatti et al., Mol. Biol. Med, 7, pp. 199–212, 1990), human haptoglobin (see Oliviero et al., Embo J. 6, (7), pp. 1905–12, 1987) and in other genes coding for additional acute phase proteins induced by IL-6 (see Heinrich et al., Biochem. J., 265, pp. 621–36, 1990), leading to the definition of a core consensus sequence CTGGGAW or CTGGRAA, where W stands for A or T, and R stands for A or G.

Hocke et al. (Mol. Cell. Biol., 12, (5), pp. 2282–94, 1992) indicated that multiple related core sequences, similar to the core sequence mentioned above, might be present in regulatory regions of wild-type genes responding to IL-6 and that this multiplicity leads to amplification of the response, as functionally analyzed with a reporter gene assay.

Wegenka et al. (Mol. Cell. Biol., 13, (1), pp. 276–88, 1993) have recently indicated an enlarged version of the core consensus sequence as the Acute Phase Response Element (APRE), active in hepatoma cells that can be represented by the formula KTMYKGKAA, wherein M stands for C or A, K stands for T or G, Y stands for C or T.

By Yuan et al. (Mol. Cell. Biol., 14, (3), pp. 1657–68, 1994) it has been shown that such APRE-like sequences bind a protein transcription factor having a molecular weight of about 90 KD, called APRF which has been recently cloned (see Akira et al., Cell, 77, pp. 63–71, 1994). In practice, the binding of activated APRF to APRE sequences would therefore lead to activation of IL-6-inducible genes (containing such APRE sequences) in IL-6-responsive cells.

As a consequence of this, an APRE element can be used as enhancer of a target gene in IL-6 responsive cells in the following way: in IL-6 responsive cells, the treatment with IL-6 induces the synthesis of APRF proteins, which bind to the APRE element, and such binding activates the expression of the target gene.

Serlupi Crescenzi et al. (Poster at the 12th European Imunol., Meeting, Barcelona, Jun. 14–17, 1994) have shown that an 8-fold repetition of the APRE DNA sequence (M8) is responsible for a 50–100 fold induction by IL-6 of a reporter gene in HepG2 human hepatoma cells.

SUMMARY OF INVENTION

The main object of the present invention is a nucleotide sequence which is able to inhibit the IL-6 activity, that comprises:

i) at least one nucleotide sequence that is an APRE element of general formula ZXMYKGKAA, wherein Z represents T or G or can also be absent, X represents T or can also be absent, M represents C or A, Y represents C or T and K represents T or G, in conjunction with ii) at least one nucleotide sequence constituting a transcription factor binding site other than the APRE element, such as those present in promoter regions.

Examples of these latter type of nucleotide sequences include: TATA box, and the binding sites for transcription factors, such as AP-1 (see Riabowol et al., PNAS USA, 89, pp, 157–61, 1992), AP-2, HNF-1 (see Clusel et al., Nuc. Ac. Res., 21 (15), pp. 3405–11), SP-1 (see Wu et al., Gene, 89, pp. 203–9, 1990), NF-icB (see Bielinska et al., Science, 250, pp. 997–1000, 1990), Oct-1, E-2 and SRF transcription factors.

In a preferred embodiment of the present invention, both the APRE element (i) and/or the nucleotide sequence (ii) of the above general formula are each repeated at least 2 times, more preferably, from 3 to 10 times, still more preferably 8 times.

In a further preferred embodiment of the present invention, the element (i) comprises at least two different APRE elements and/or the nucleotide sequence (ii) comprises at least two different oligonucleotide sequences constituting a transcription factor binding site other the APRE element.

The nucleotide sequence (ii) is preferably the SV40 early promoter.

The APRE element (i) comprises, for example, the following nucleotide sequence: TTCTGGGAA.

Figure 2:
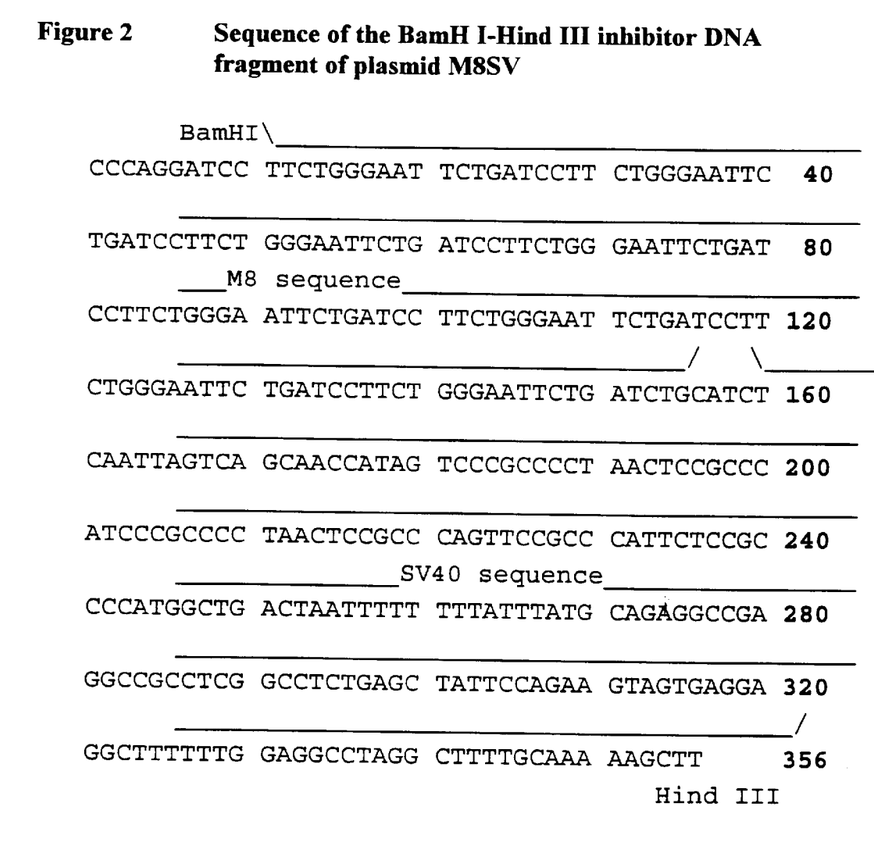
FIG. 2. Sequence of the BamH I-Hind III inhibitor DNA fragment of plasmid pM8SV. The continuous line above the upper part of the shown nucleotide sequence represents the M8 sequence. The bold continuous line above the lower part of the nucleotide sequence represents the SV40 promoter sequence. BamH I and Hind III restriction sites are also indicated.

FIG. 2 reports a nucleotide sequence which falls within the scope of the invention, in accordance with its preferred embodiments. Such nucleotide is also reported as SEQ ID NO: 1 and it constitutes one object of the invention.

A further object of the present invention is a plasmid vector containing the nucleotide sequence of the invention.

An additional aspect of the present invention is the use of the nucleotide sequence of the invention as a therapeutic tool to inhibit the action of IL-6, in those conditions where IL-6 plays a pathological role.

The present invention also provides pharmaceutical compositions comprising a nucleotide sequence or a plasmid vector according to the invention. Such compositions can be formulated for oral, rectal, intravenous or topical use. Formulations of the present invention may include the use of any combination of viral-mediated gene transfer, liposome formulation, receptor-mediated DNA delivery and/or dumbbell structures of the active nucleotide inhibitory sequence according to the invention.

The inhibitory action of the nucleotide sequence of the invention has been determined with a reporter gene assay.

The reporter gene assay of the invention is based on the ability of the APRE element to function as enhancer of any gene in IL-6 responsive cells (as reported above). In this case, the APRE element is used as enhancer of a target reporter gene (which is, for example, the Luciferase gene) in IL-6 responsive cells (which are, for example, hepatic cells such as HepG2). The cells are then treated with IL-6: if enough of the APRF proteins produced are captured by an excess of the nucleotide sequence of the invention, the target gene will not be activated.

According to this assay, inhibitor plasmids are constructed, which contain the nucleotide sequence of the invention. An example of such plasmids is reported in FIG. 1 together with its construction strategy.

This and other plasmids, containing the nucleotide sequence of the invention, are also intended to constitute a further embodiment of the invention.

The invention will now be described by means of the following Examples, which should not be construed as in any way limiting the present invention. The Examples will refer to the Figures specified here below.

BRIEF DESCRIPTION OF THE DRAWINGS

FIG. 1. Construction strategy of plasmid pM8SV. pM8SVL is digested with Sal I and Hind III and the sticky ends are transformed in blunt ends by the Kleenow reaction. The resulting 3.2 Kb DNA fragment is purified by agarose gel electrophoresis, then it is self-ligated Plasmid pM8SV is thus generated, containing the M8 sequence (about 170 bp) and the sequence from the SV40 virus early promoter (about 190 bp), but lacking the luciferase gene.

DETAILED DESCRIPTION OF THE INVENTION

EXAMPLE 1

Construction of plasmids. An IL-6-responding luciferase reporter gene plasmid was constructed by first preparing through chemical synthesis a double-stranded oligonucleotide of 38 bp with an uncut BamH I site at its 5' blunt end, and a protruding lower strand of 4 nucleotides compatible with the Bgl II and BamH I sites at the 3' end. This synthetic oligonucleotide was named M2 and it contained two identical APRE sequences from the rat α2-macroglobulin gene promoter region. The sequence of the oligonucleotide (upper strand, 5' to 3') was as follows:

GGATCCTTCTGGGAATTCTGATCCT-TCTGGGAATTCTG (SEQ ID NO: 2). This oligonucleotide was cloned in the Sma I-Bgl II sites of plasmid pGL2-pv (from Promega Corporation), where the expression of the luciferase reporter gene is driven by the SV40 virus early promoter, thus forming, after self-ligation, plasmid pM2SVL.

The synthetic oligonucleotide, through its 5' blunt end, was also ligated to the Sma I site of the same plasmid pGL2-pv and the resulting linear ligation product was then cut with Hind III. The resulting linear vector was used as a recipient to clone the following DNA fragments: 1) the BamH I-Hind III fragment of 238 bp from plasmid pM2SVL, thus forming, after self-ligation, plasmid pM4SVL; 2) the BamH I-Hind III fragment of 280 bp from pM4SVL, thus forming, after self-ligation, plasmid pM6SVL and 3) the BamH I-Hind III fragment of 322 bp from pM6SVL, thus forming, after self-ligation, plasmid pM8SVL.

Plasmid pM8L was constructed by digesting pM8SVL with Sfan I and by converting the sticky ends in blunt ends by fill-in reaction with the Kleenow enzyme. After BamH I digestion, the resulting M8 DNA fragment of 163 bp was ligated with a 16 bp BamH I-Kpn I synthetic adapter and cloned in a 5.6 Kb DNA fragment resulting from Sma I+Kpn I digestion of the pGL2-b vector (from Promega Corporation). Plasmid pGL-2b is identical to the above-mentioned pGL2-pv plasmid, except for the absence of the SV40 promoter sequence in pGL2-b. The 16 bp adapter contained a multiple cloning site, and it was prepared by chemical synthesis with the following sequence:

upper strand: 5'CGCGGCCGCCTCGAGG3' (SEQ ID NO: 3);
lower strand: 5'GATCCCTCGAGGCGGCCGCGGTAC3' (SEQ ID NO: 4).

The plasmid resulting from the above construction was pM8L, and it had the M8 DNA sequence without promoter, embedded in a multiple cloning site, upstream to the luciferase gene.

The luciferase reporter gene plasmid pM8TKL was prepared by cutting plasmid pGEM-TK-CAT (described in Cohen et al., EMBO J., 7(5), pp. 1411–9, 1988) with Xba I and Bgl II. The resulting 181 bp fragment containing the TK promoter sequence of the viral HSV thymidine kinase gene was ligated with the 5.8 Kb Nhe I-Bgl II fragment of the pM8L vector, between the M8 and the luciferase DNA sequences.

The luciferase reporter gene plasmid pHPSVL was constructed first by PCR amplification of 841 bp from the haptoglobin gene promoter region from human genomic DNA. The 3' end of the amplified PCR fragment corresponded to position −36 from the transcription start of the human haptoglobin gene (as reported in Maeda et al., J. Biol. Chem., 260(11), pp. 6698–709, Jun. 10, 1985). This PCR product was prepared with upper and lower primers containing respectively Mlu I and Bgl II restriction sites. The DNA primers synthesised for genomic amplification of the haptoglobin promoter region had the following sequence:

upper primer: 5'CTACGCGTGCAGTATTGACCCTTC-CTCCT3' (SEQ ID NO: 5);
lower primer: 5'CGCAGATCTAGCTCACTTCTC-CCCCTTC3' (SEQ ID NO: 6).

The PCR fragment thus obtained was inserted in Mlu I and Bgl II sites of the luciferase reporter gene plasmid pGL2-pv mentioned above, upstream to the SV40 early promoter. The resulting plasmid was pHPSVL.

In order to construct the inhibitor plasmid pM8, the above plasmid pM8L was digested with Sal I and Bgl II and the sticky ends thus generated were repaired in blunt ends by the Kleenow reaction. The resulting fragment of 3.1 Kb, lacking the luciferase gene sequence, was purified by agarose gel electrophoresis, then it was self-ligated to generate the inhibitor plasmid pM8.

Figure 1:
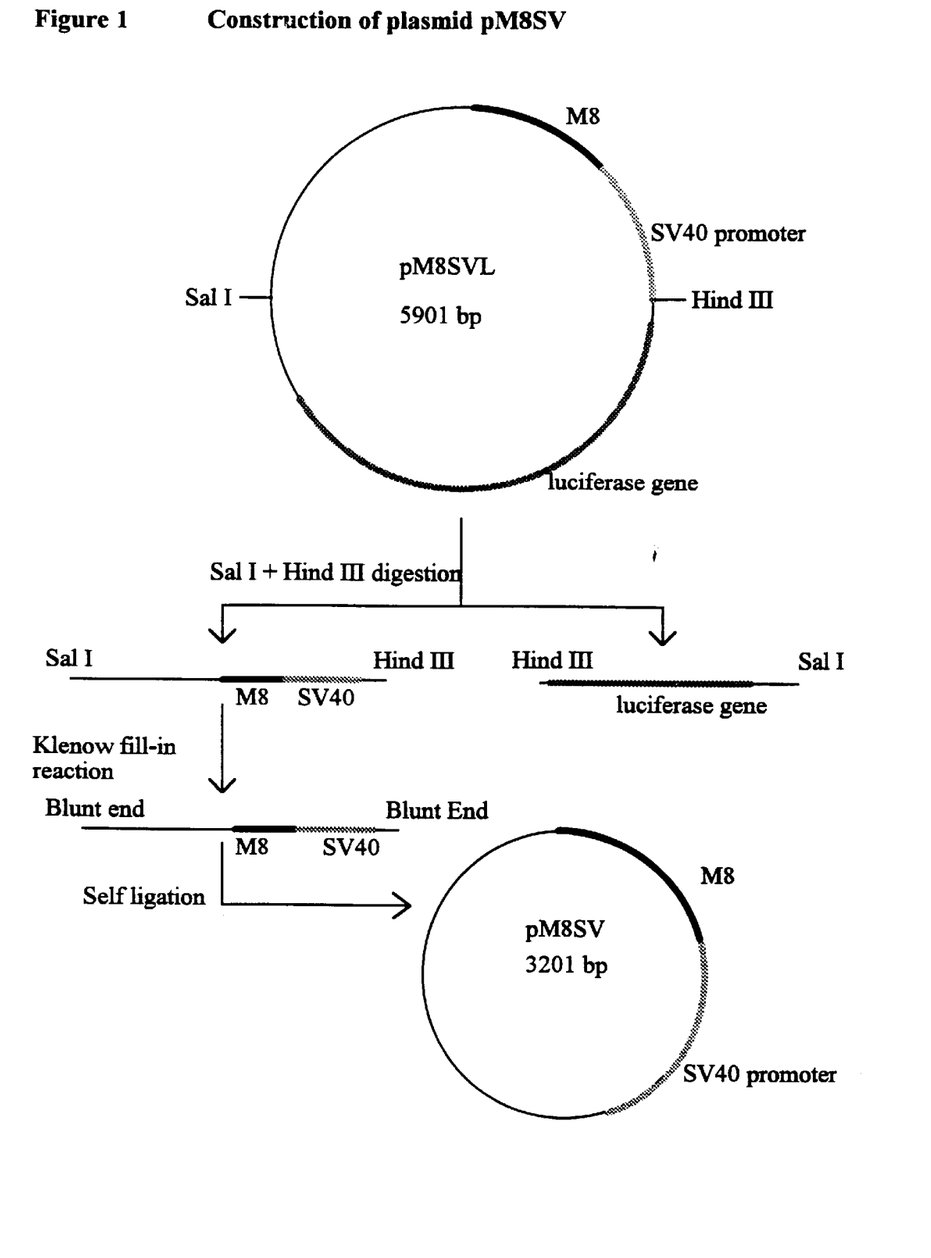

The inhibitor plasmid pM8SV was prepared as shown in FIG. 1. pM8SVL was digested with Sal I and Hind III and the sticky ends were transformed in blunt ends by the Kleenow reaction. The resulting 3.2 Kb DNA fragment was purified by agarose gel electrophoresis, then it was self-ligated. Plasmid pM8SV was thus generated, containing the M8 sequence (about 170 bp) and the sequence from the SV40 virus early promoter (about 190 bp), but lacking the luciferase gene.

The inhibitor plasmid pSV was constructed by cutting out the Sal I-Hind III fragment containing the luciferase gene from plasmid pGL2-pv mentioned above. The resulting fragment of 3.1 Kb was subject to fill-in reaction with the Kleenow enzyme, purified by agarose gel electrophoresis and then it was self-ligated, thus yielding plasmid pSV which contains the SV40 promoter but lacks the luciferase gene.

The carrier plasmid pC was prepared by cutting plasmid pGL2-b mentioned above with Sal I and Hind III restriction enzymes. The resulting fragment of 2.9 Kb was subject to fill-in reaction with the Kleenow enzyme, purified by agarose gel electrophoresis and then it was self-ligated, thus yielding plasmid pC.

All plasmid constructs described above were used to transform the E. Coli strain XL1-Blue with standard techniques (Ausubel R. et al., Current Protocols in Molecular Biology. Greene Publishing Associates and Wiley Interscience, New York). Plasmid DNA was extracted from transformed clones by minipreparative alkaline lysis method (according to Ausubel, above). Plasmid DNA was controlled by restriction analysis and by agarose gel electrophoresis. Clones with the expected pattern were selected. To obtain purified plasmid preparations to be used in transfection of mammalian cells, 300 ml cultures of the selected E. Coli XL1-Blue transformants were prepared. The plasmids were then purified by QIAGEN tip 500 ion-exchange minicolumns, by following the manufacturer instructions.

EXAMPLE 2

Cell lines and culture conditions. HepG2 human hepatoma cells (ATCC) were cultured in MEM supplemented with 10% FCS, 5 mM L-glutamine, 20 mM HEPES, 100 U/ml penicillin/streptomycin. T47D human breast carcinoma cells (ATCC) were cultured in DMEM supplemented with 10% FCS, 5 mM L-glutamine, 20 mM HEPES, 100 U/ml penicillin/streptomycin. M1 mouse myeloid leukaemia cells (ATCC) were cultured in RPMI supplemented with 10% FCS, 5 mM L-glutamine, 20 mM HEPES, 100 U/ml penicillin/streptomycin. Culture of the above cell lines was performed in the presence or absence of the appropriate dose of IL-6 (CHO-derived h IL-6 from Interpharm Laboratories), as specified below.

EXAMPLE 3

Transient transfections and luciferase and β-galactosidase assays. Transient transfection of HepG2 human hepatoma cells and T47D human breast carcinoma cells was carried out using calcium phosphate-DNA precipitation in hepes buffer, according to standard procedures (Ausubel R. et al., Current Protocols in Molecular Biology. Greene Publishing Associates and Wiley Interscience, New York). Transient transfection of mouse M1 myeloid leukaemia cells was performed using DEAE-dextran, according to standard procedures (according to Ausubel, above).

In order to detect luciferase and β-galactosidase activities, cells were extracted in situ by incubation for 15 minutes at room temperature with 1 ml/$10^6$ cells of extraction buffer (25 mM TRIS-phosphate pH 7.8, 2 mM DTT, 2 mM EDTA, 10% glycerol, 1% Triton X-100). For luciferase activity, 20 μl of cell extract were directly assayed with 100 μl of luciferase assay buffer (20 mM Tricine, 1.07 mM ($MgCO_3$) $_4Mg(OH)_2.5H_2O$, 2.67 mM $MgSO_4$, 0.1 mM EDTA, 33.3 mM DTT, 0.27 mM CoenzymeA, 0.47 mM luciferin, 0.53 mM ATP). For β-galactosidase activity, 10 μl of cell extract were incubated for 1 hour at 37° C. with 100 μl of Lumigal substrate (from Lumigen). Lumigal and luciferase readings were performed with a Berthold Autolumat LB953 luminometer, the output being counts per seconds (cps) integrated over a period of 30 seconds for luciferase and 15 seconds for β-galactosidase.

Reporter plasmid pM8SVL was shown to confer IL-6 responsiveness after transient transfection of HepG2 cells, by increasing up to 50–100 times the expression of luciferase activity (Serlupi Crescenzi et al., Poster at the 12th European Immunol., Meeting, Barcelona, Jun. 14–17, 1994).

This plasmid was also tested in T47D human breast carcinoma cells and in mouse M1 myeloid leukaemia cells. M1 cells were transfected with 0.5 μg DNA/10$^6$ cells using DEAE/Dextran, while 2.5 μg DNA/10$^5$ cells were used for calcium phosphate transfection of T47D cells.

Figure 3:
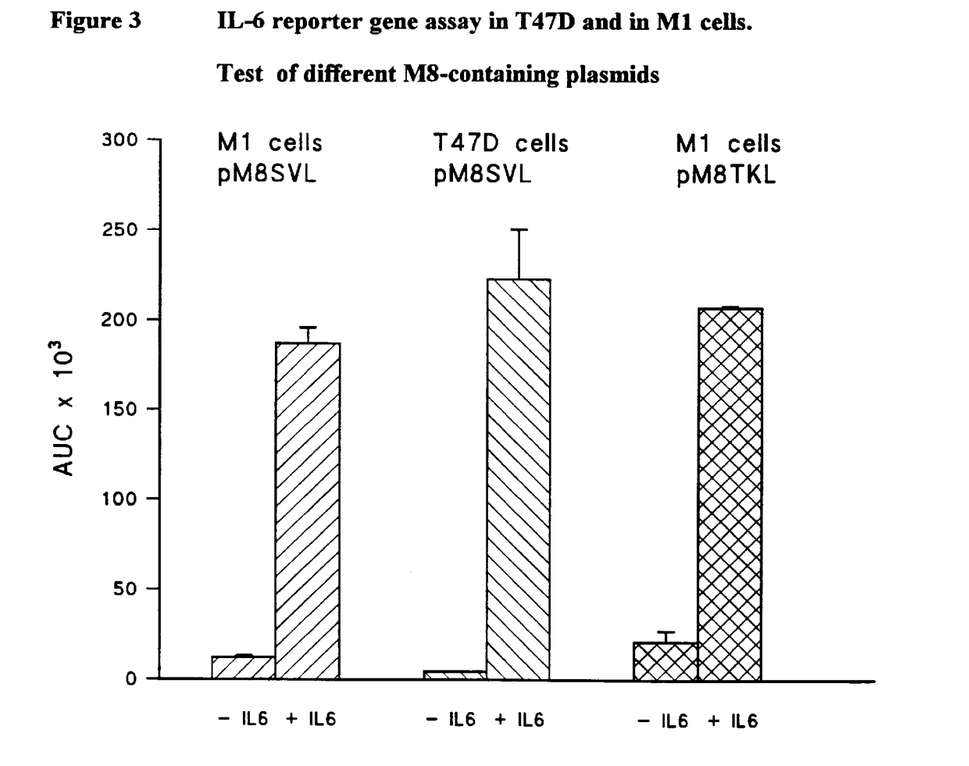
FIG. 3. IL-6 reporter gene assay in T47D and M1 cells. Test of different M8-containing plasmids. Reported values of light emission are averages of duplicate determinations of cps integrated over a period of 30 seconds (AUC=Area Under the Curve) from transfected cells. Each bar represents the average of three transfections ±SEM.

Only very limited features are shared by these two cell lines, apart from their common response to human IL-6. Results (FIG. 3) showed that he M8 DNA molecule in pM8SVL plasmid was significantly active in both ell lines after IL-6 treatment. As shown in FIG. 3, a significant response to IL-6 was also observed in M1 cells with the reporter gene plasmid pM8TKL, where the M8 molecule was flanked by the thymidine kinase promoter, which is different from the SV40 promoter present in pM8SVL.

Figure 4:
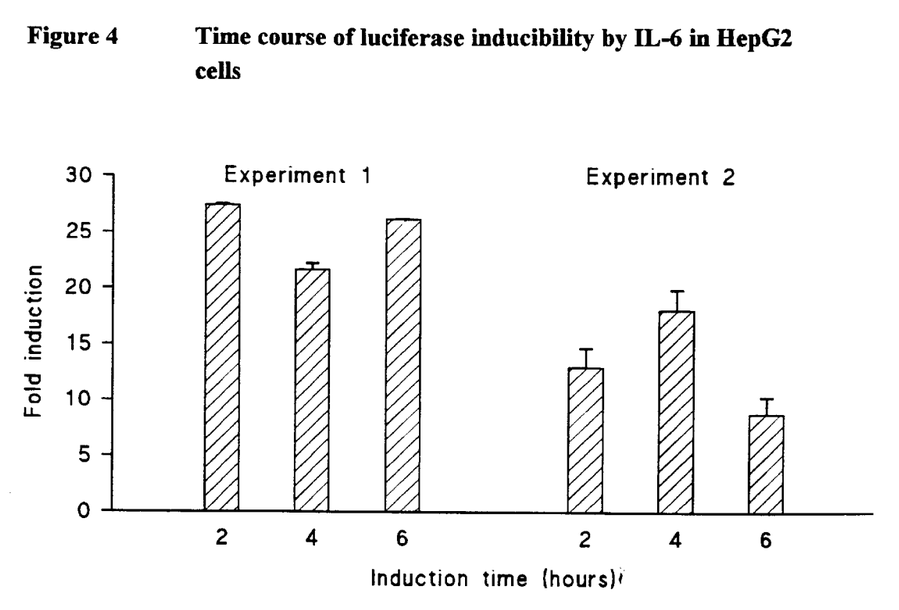
FIG. 4. Time-course of luciferase inducibility of transfected Hep G2 cells after treatment with IL-6. Plasmid pM8SVL was used as the positive reporter gene plasmid. Each bar represents the average of two transfections ±SEM. Two experiments are shown in the Figure.

Time-course of luciferase inducibility of transfected HepG2 cells has been tested after treatment with IL-6 (1 ng/ml). Plasmid pM8SVL was used as positive reporter gene plasmid (at 0.2 μg/10$^5$ cells). Cells were transfected overnight, splitted and then exposed to the IL-6 treatment. The results are reported in FIG. 4 and they show that almost full response to IL-6 could be achieved after only two hours of IL-6 treatment.

EXAMPLE 4

Test of inhibitor plasmid pM8. Inhibition of IL-6 activity by M8 DNA molecules was measured after co-transfection in HepG2 cells of i) the pM8SVL reporter gene plasmid responding to IL-6 and ii) the M8 molecule inserted in the pM8 inhibitor plasmid. This latter plasmid hosts the M8 sequence but it has not the ability to confer responsiveness to IL-6. HepG2 cells were transfected with up to 2.5 μg/10$^5$ cells of the IL-6-responding reporter plasmid pM8SVL (containing M8 and the luciferase gene) and 10 or 50 fold molar excess of pM8, in the presence of various doses of IL-6. The total amount of DNA per transfection was kept constant with the use of the carrier plasmid pC, which is identical to pM8, except for the absence in the former plasmid of the specific 165 bp-long M8 DNA fragment.

Figure 5:
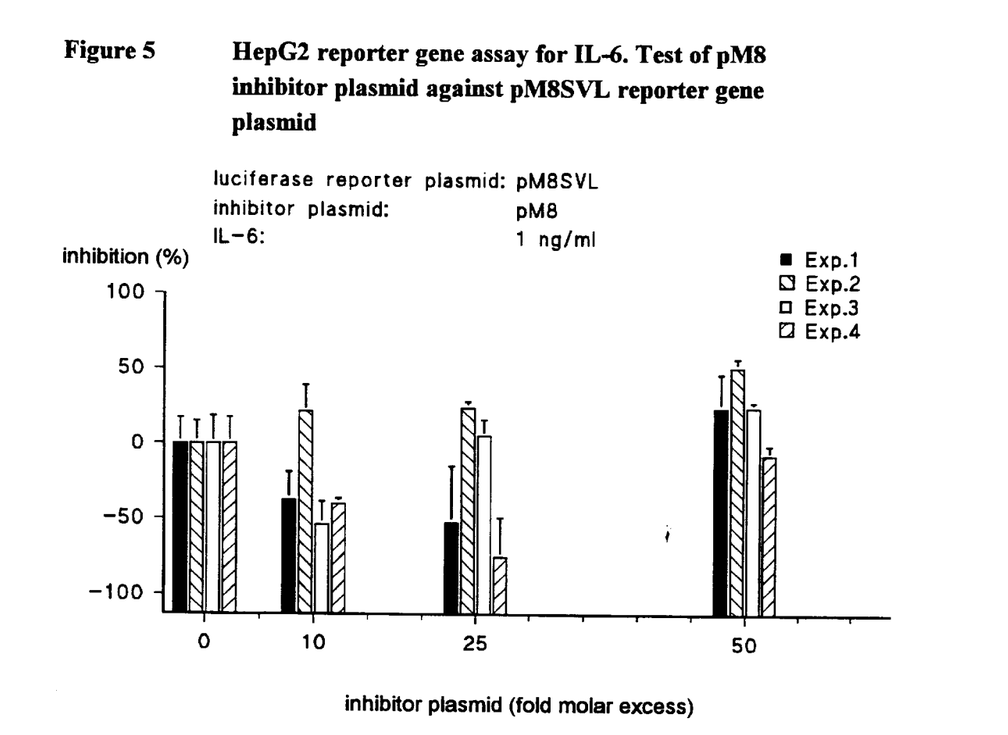
FIG. 5. HepG2 reporter gene assay for IL-6. Test of pM8 as inhibitor plasmid against pM8SVL as reporter gene plasmid. Each bar represents the average of three transfections ±SEM. Four experiments are shown in the Figure.

As reported in FIG. 5, the inhibitor plasmid did not show significant and reproducible specific inhibition of the IL-6 activity in four experiments, even at 50 fold molar excess of the pM8 inhibitor plasmid. In these experiments the IL-6-responding reporter gene plasmid pM8SVL was used at a dose of 0.1 μg/10$^5$ cells, while the constant amount of total DNA used in transfection was 5 μg/10$^5$ cells. The suboptimal dose of IL-6 used in these experiments was 1 ng/ml. As shown in FIG. 5, variability was acceptable with these experimental conditions, given the fact that distinct transfections per se are an inevitable source of variability.

EXAMPLE 5

Test of inhibitor plasmid pM8SV. The results reported in FIG. 5 were somewhat surprising, because the active M8 inhibitor DNA sequence of the inhibitor plasmid pM8 is identical to the active sequence of the pM8SVL reporter gene plasmid. After co-transfection, competition between these two identical M8 sequences present in different plasmids would therefore be expected, resulting in inhibition of IL-6 activity in the reporter gene assay.

Moreover, the results described above can not be explained by the presence of an excess of activated, IL-6-specific transcription factor(s), which are not sufficiently neutralised by the M8 inhibitor DNA molecules, since the data were obtained in the presence of a limiting amount of IL-6. In addition, published data on similar experiments with DNA binding sites for known transcription factors (26–30) are not consistent with the results reported in FIG. 5.

An alternative explanation for the results shown in FIG. 5 could be that sequences other than M8 in the reporter gene plasmid may contribute to the IL-6-specific signal transduction. These sequences should be missing in the pM8 inhibitor plasmid, but they should be present in the positive reporter gene plasmid pM8SVL (e.g., sequences of the SV40 early gene promoter, which can bind general transcription factors). The inhibitor plasmid pM8 would therefore be ineffective in competing with the reporter gene plasmid pM8SVL.

In order to test this hypothesis, an inhibitor plasmid (pM8SV) was constructed, containing as IL-6-inhibitor DNA sequences, both the M8 sequence and the SV40 promoter sequence (see FIG. 1). This inhibitor plasmid was tested in the IL-6 reporter gene assay with HepG2 cells. Four independent experiments were performed, with duplicate transfections per experiment. Transfections were performed with 0.1 μg of reporter plasmid DNA and the molar excess of inhibitor plasmid shown in FIG. 6. The total amount of transfected DNA was kept constant with the carrier plasmid Transfected cells were treated for 18 hours with 1 ng/ml of IL-6.

Figure 6:
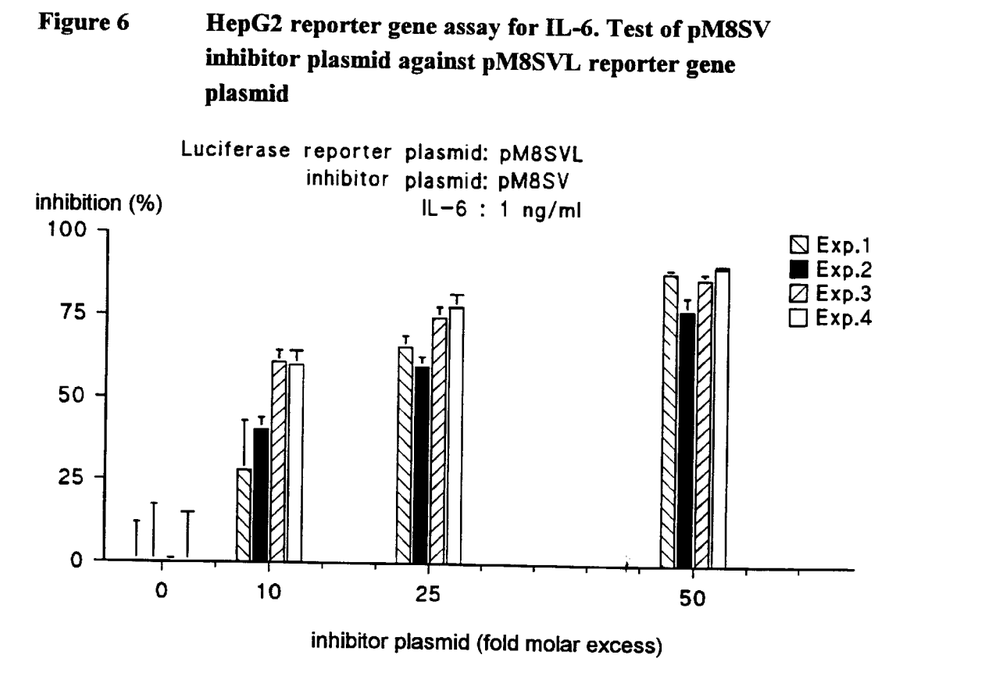
FIG. 6. HepG2 reporter gene assay for IL-6. Test of pN8SV as inhibitor plasmid against pN8SVL as reporter gene plasmid. each bar represents the average of three transfections ±SEM. Results are expressed as % of inhibition with respect to HepG2 cells transfected with carrier plasmid pC without inhibitor plasmid.

Results, shown in FIG. 6, indicated a clear dose-dependent inhibition of IL-6 activity by the pM8SV inhibitor plasmid. Raw data of FIG. 6 are reported are reported on Table 1. Three replicate transfections per dose of inhibitor plasmid were performed in each experiment. For each experiment, the induced and non-induced values shown in a single row come form the same transfection. Reported values of light emission are cps integrated over a period of 30 seconds. As it can be seen from such Table 1, some variability was observed in these experiments, especially at lower doses of the inhibitor plasmid, but usually CVs of replicate transfections were well below 20%.

In order to rule out that the inhibition of IL-6 activity provided by the pM8SV inhibitor plasmid was due exclusively to the SV40 promoter DNA sequence and not to the combination of M8 and SV40 sequences, an additional inhibitor plasmid was constructed and tested in the reporter gene assay. This plasmid contained only the SV40 DNA sequence as inhibitor of IL-6 activity, without the M8 inhibitor sequence, nor the luciferase gene.

Figure 7:
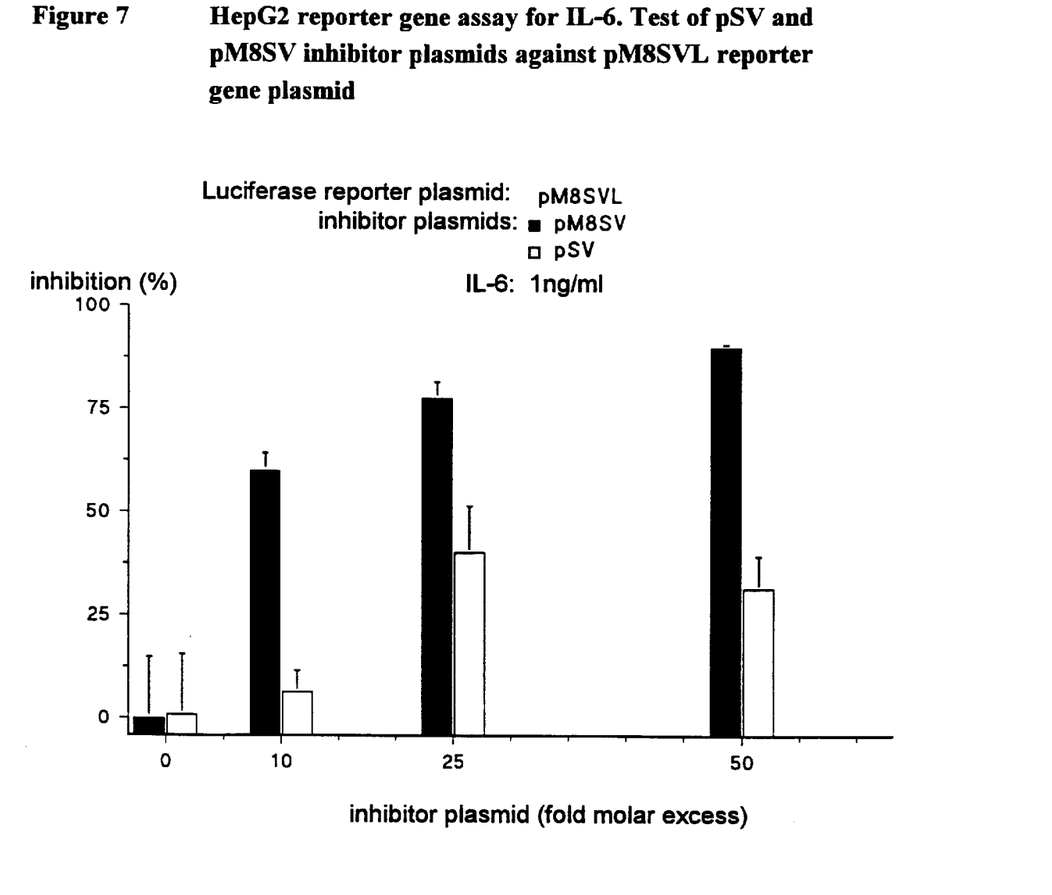
FIG. 7. HepG2 reporter gene assay for IL-6. Test for pSV and pM8SV as inhibitor plasmids against pN8SVL reporter gene plasmid. Each bar represents the average of three transfections ±SEM. Results are expressed in % of inhibition with respect to HepG2 cells transfected with carrier plasmid pC without inhibitor plasmid.

Transfections were performed with 0.1 μg of reporter plasmid DNA and the molar excess of inhibitor plasmid shown in FIG. 7. The total amount of transfected DNA was kept constant with the carrier plasmid. Transfected cells were treated for 18 hours with 1 ng/ml of IL-6. The results, reported in FIG. 7, show that this inhibitor plasmid (pSV) displayed only partial inhibition of IL-6 activity, which never resulted to be above 40% and was not dose-dependent. This allows to conclude that the SV40 DNA sequence alone was not sufficient for effective inhibition of IL-6 activity. On the other hand, the luciferase-containing reporter plasmid pCL2-pv contains the SV40 promoter sequence but not the M8 sequence, thus resulting in a basal level of luciferase expression not further inducible by IL-6. In this plasmid, the basal level of luciferase expression was not inhibited by the pM8SV inhibitor plasmid, thus showing that transcription factors which are specifically bound only to the SV40 promoter region of pGL2-pv, are not effectively removed by the pM8SV inhibitor plasmid. In fact, in the presence of the latter inhibitor plasmid, luciferase activity from the reporter plasmid pGL2-pv was even higher than in the absence of the inhibitor plasmid (not shown).

EXAMPLE 6

Inhibition by pM8SV of the IL-6 activity conferred by the reporter gene plasmid pHPSVL. We then wanted to test the inhibitor plasmid pM8SV in an additional reporter gene assay for IL-6, where the target DNA sequence mediating the IL-6 signal in the reporter gene plasmid is not perfectly matching the M8 inhibitor sequence. HepG2 cells were therefore transfected with plasmid pHPSVL, which contains 841 base pairs from the promoter sequence of the human haptoglobin gene, flanked by the SV40 promoter and the luciferase gene. One APRE site from the haptoglobin promoter sequence (according to Maeda et al., J. Biol. Chem., 260(11), pp. 6698–709, Jun. 10, 1985) is present in this plasmid. We have previously shown that this plasmid does respond to IL-6 by a 6–8-fold increase of luciferase expression (Serlupi Crescenzi et al., Poster at the 12th European Immunol., Meeting, Barcelona, Jun. 14–17, 1994).

Figure 8:
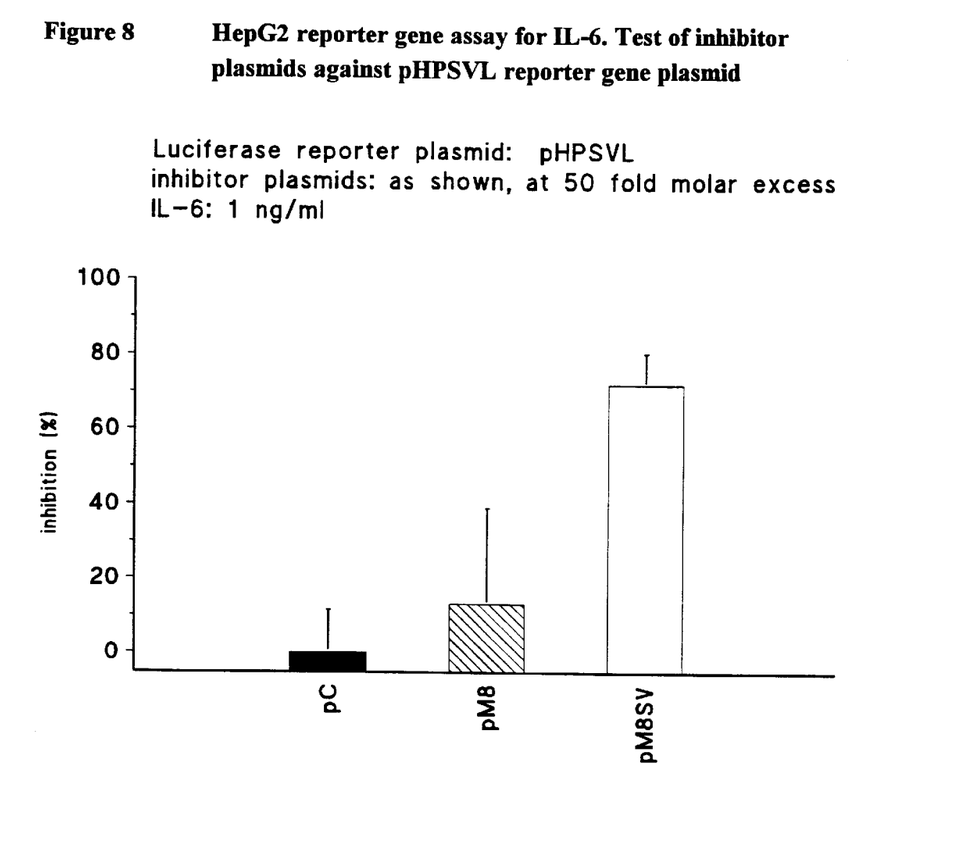
FIG. 8. inhibition test of IL-6 activity by inhibitor plasmids pM8 and pM8SV in a HepG2 reporter gene assay based on the luciferase gene under control of the IL-6 inducible regulatory sequences from the human haptoglobin gene promoter. Each bar represents the average of three transfections ±SEM Results are expressed in % of inhibition with respect to HepG2 cells transfected with carrier plasmid pC without inhibitor plasmid. Transfections were performed with 0.1 μg of reporter plasmid DNA and the shown molar excess of inhibitor plasmid. The total amount of transfected DNA was kept constant with the carrier plasmid. Transfected cells were treated for 18 hours with 1 ng/ml of IL-6.

Results from one experiment of triplicate transfections are shown in FIG. 8. After co-transfection of the reporter gene plasmid pHPSVL with 50-fold molar excess of the carrier plasmid, inducibility by IL-6 resulted in about 4-fold higher luciferase expression with respect to the basal level. On the contrary, co-transfection with 50-fold molar excess of the inhibitor plasmid pM8SV completely abolished the inducibility by IL-6. The pM8SV inhibitor plasmid was therefore able to inhibit IL-6 activity also when an IL-6-responding reporter gene plasmid different from pM8SVL was tested (e.g., the reporter plasmid pHPSVL).

EXAMPLE 7

Test of inhibitor plasmid pM8SV in T47D cells. The pM8SV inhibitor plasmid was also tested in the pM8SVL reporter gene assay, using T47D human breast carcinoma cells, where the transduction of the IL-6 signal might be different than in hepatoma cells. As previously mentioned, the IL-6 reporter gene assay with the pM8SVL reporter gene plasmid is working on this cell line, although it is not optimised. Since sensitivity of the assay is somewhat lower with T47D cells, transfections were performed with 1 μg of the positive reporter gene plasmid/$10^5$ cells, which is a relatively high level of plasmid DNA. Non-specific inhibition was therefore observed in this experiment in the presence of excess carrier or inhibitor plasmid, resulting in higher variability of the IL-6-specific inhibition.

The results are shown in Table 2. Averages (AVG) and standard deviations (SD) of triplicate transfections from two experiments are shown.

Average values of fold induction are calculated from the raw values of each transfection. 1 and 0.5 μg of reporter gene plasmid were used in experiments 1 and 2 respectively per $10^5$ transfected cells.

Separate transfections of carrier plasmid and inhibitor plasmids were performed in these experiments, both plasmids being used at the indicated molar excess with respect to the reporter plasmid.

After transfection cells were induced for 18 hours with 1 ng/ml of IL-6. Reported values of light emission are cps integrated over a period of 30 seconds. IL-6 specific inhibition in these experiments was evaluated by comparing the induction obtained in the presence of excess of inhibitor plasmid with the induction obtained in the presence of the corresponding dose of carrier plasmid.

Moreover, because of non-specific inhibition, the basal level of luciferase expression was close to the quantitation limit of the assay. Results, reported in Tab. 2 (see Experiment 1) showed that, after triplicate transfections, relevant, specific inhibition of IL-6 activity was obtained at 20-fold molar excess of inhibitor plasmid pM8SV, but not at 10-fold molar excess. A 50-fold molar excess of the inhibitor plasmid could not be tested in this experiment, because non-specific inhibition became too high.

These results could not be reproduced in an additional experiment, when 0.5 μg DNA/$10^5$ cells were used (Tab. 2, see Experiment 2). The reason for this lack of reproducibility can be due to the relatively high variability and low sensitivity of the T47D reporter gene assay. Alternatively, differential target cell selectivity could explain these results.

EXAMPLE 8

Definition of the minimal DNA inhibitory sequence. In order to identify the minimal DNA sequence which retains the ability to inhibit the binding of transcription factors relevant for IL-6 inducibility, the experimental approach of electrophoretic mobility shift assay (EMSA) can be used (according to Ausubel). A test for functional inhibition imparted by this minimal sequence can be set using the reporter gene assay mentioned in Example 3 and following Examples. The miimal DNA sequence we have shown to functionally inhibit IL-6 activity in a reporter gene assay was the BamH I-Hind III fragment of 350 bp of the inhibitor plasmid pM8SV, which contains an 8-fold repetition of an APRE DNA sequence and the SV40 early promoter sequence. This latter sequence is known to contain binding sites for general transcription factors such as an AP-1-like site (as reported in Zenke et al., EMBO J., 5(2), pp. 387–97, 1986) and a 6-fold repetition of the Sp-1 site (as reported in Dynan et al., Cell, 35, pp. 79–87, 1983). The BamH I-Hind III DNA fragment can be deleted at its 5' and/or 3' ends, by conventional means such as PCR or nuclease treatment (according to Ausubel) in order to contain, e.g., two APRE sequences and only a single or a few binding site for specific transcription factors from the SV40 early promoter. The resulting DNA sequences can be used for inhibition tests of the pSVM8L-based reporter gene assay in HepG2 cells.

Furthermore, a minimal DNA fragment which retains full ability to functionally inhibit the IL-6 signal can be used in EMSA, by labelling this DNA with a $^{32}$P nucleotide through conventional means, such as end-labelling or fill-in Kleenow reactions. The resulting labelled DNA fragment can be incubated with nuclear extracts from HepG2 cells after IL-6 treatment.

Increasing amounts of a competitor DNA sequence can also be co-incubated, such as anyone of the unlabelled DNA fragments which resulted from the above-mentioned deletions of the BamH I-Hind III inhibitor DNA fragment. After incubation, the mixture can be run in non-denaturing polyacrylamide gel electrophoresis. The binding of relevant transcription factors to the tested labelled DNA fragment will be revealed by a shift in the gel mobility (retardation) expected for the unbound, labelled DNA The inhibition of this binding in the presence of competitor, unlabelled DNA sequences will be revealed by the specific disappearance of the shifted gel bands.

TABLE 1

HepG2 reporter gene assay for IL-6.
Test of pSVM8 inhibitor plasmid against pSVM8L reporter gene plasmid

| Fold mol. excess of inhibitor | Experiment 1 | | Experiment 2 | | Experiment 3 | | Experiment 4 | |
|---|---|---|---|---|---|---|---|---|
| | − IL-6 | + IL-6 | − IL-6 | + IL-6 | − IL-6 | + IL-6 | − IL-6 | + IL-6 |
| 0 | 30.330 | 1.562.000 | 49.200 | 1.664.000 | 30.880 | 2.489.000 | 37.430 | 1.587.000 |
| | 34.760 | 1.227.000 | 83.590 | 1.914.000 | 47.610 | 2.266.000 | 34.000 | 1.433.000 |
| | 32.920 | 1.711.000 | 91.560 | 1.754.000 | 49.670 | 3.239.000 | 31.130 | 1.362.000 |
| 10 | 29.400 | 751.800 | 144.300 | 2.380.000 | 33.680 | 923.100 | 32.390 | 476.200 |
| | 34.660 | 951.300 | 161.500 | 2.202.000 | 35.020 | 722.500 | 39.610 | 790.400 |
| | 24.530 | 1.159.000 | 129.200 | 1.953.000 | 37.620 | 1.110.000 | 32.770 | 516.900 |
| 25 | 40.730 | 568.100 | 85.410 | 745.300 | 46.760 | 538.400 | 36.790 | 298.100 |
| | 45.320 | 677.700 | 61.340 | 671.600 | 33.520 | 414.000 | 20.320 | 255.500 |
| | 32.670 | 620.400 | 71.040 | 773.300 | 27.950 | 543.500 | 26.080 | 318.800 |
| 50 | 53.210 | 312.200 | 148.700 | 857.900 | 23.820 | 173.500 | 120.800 | 586.000 |
| | 60.110 | 268.500 | 159.700 | 655.300 | 25.370 | 150.500 | 96.900 | 716.400 |
| | 73.810 | 427.300 | 68.630 | 517.500 | 46.470 | 287.500 | 195.800 | 1.029.000 |

TABLE 2

T47D reporter gene assay for IL-6

| Fold molar excess of inhibitor or carrier plasmid | | | 10 | | 20 | |
|---|---|---|---|---|---|---|
| | | | AVG | (SD) | AVG | (SD) |
| EXP. 1 | Reporter plasmid plus carrier plasmid | −IL-6 +IL-6 Fold Induct. | 7832 423746 61 | (3795) (108679) (27) | 932 58950 68 | (141) (29703) (44) |
| | Reporter plasmid plus pM8 inhib. plasmid | −IL-6 +IL-6 Fold Induct. | 7498 570099 85 | (2848) (29927) (34) | not determined | |
| | Reporter plasmid plus pM8SV inhib. pl. | −IL-6 +IL-6 Fold Induct. | 925 98766 110 | (123) (21586) (39) | 704 11416 15 | (103) (11533) (13) |
| EXP. 2 | Reporter plasmid plus carrier plasmid | −IL-6 +IL-6 Fold Induct. | 35320 390400 15 | (20227) (45230) (11) | 2325 77617 35 | (1019) (30495) (8) |
| | Reporter plasmid plus pM8 inhib. plasmid | −IL-6 +IL-6 Fold Induct. | 7498 570099 85 | (2256) (40806) (14) | not determined | |
| | Reporter plasmid plus pM8SV inhib. pI. | −IL-6 +IL-6 Fold Induct. | 925 98766 110 | (495) (64852) (8) | 704 11416 15 | (103) (11533) (13) |

We claim:

1. A nucleotide sequence which inhibits IL-6 activity, that comprises:
   i) at least one nucleotide sequence that is an APRE element of general formula ZXMYKGKAA, wherein Z represents T or G or can also be absent, X represents T or can also be absent, M represents C or A, Y represents C or T and K represents T or G;
   ii) at least one nucleotide sequence constituting a transcription factor binding site other than the APRE element.

2. The nucleotide sequence according to claim 1, wherein (i) is the nucleotide sequence TTCTGGGAA.

3. The nucleotide sequence according to claim 1, wherein (ii) is selected from the group consisting of TATA Box, binding site for transcription factor AP-1, binding site for transcription factor AP-2, binding site for transcription factor HNF-1, binding site for transcription factor SP-1, binding site for transcription factor NF-KB, binding site for transcription factor Oct-1, binding site for transcription factor E-2, and binding site for transcription factor SRF.

4. The nucleotide sequence according to claim 1, wherein the APRE element (i) is repeated at least 2 times.

5. The nucleotide sequence according to claim 4, wherein the APRE element is repeated from 3 to 10 times.

6. The nucleotide sequence according to claim 4, wherein the APRE element is repeated 8 times.

7. The nucleotide sequence according to claim 1, wherein the sequence (i) comprises at least two different APRE elements.

8. The nucleotide sequence according to claim 1, wherein the sequence (ii) comprises at least two different oligonucleotide sequences constituting a transcription factor binding site.

9. The nucleotide sequence according to claim 8, wherein the sequence (ii) is the SV40 early promoter.

10. The nucleotide sequence according to claim 1, as reported in SEQ ID NO: 1.

11. A plasmid vector containing the nucleotide sequence of claim 1.

12. A composition comprising the nucleotide sequence according to claim 1 together with one or more pharmaceutically acceptable carriers and/or excipient.

13. A composition comprising the plasmid according to claim 11 together with one or more pharmaceutically acceptable carriers and/or excipients.

14. A method for inhibiting IL-6 activity, comprising the step of introducing the nucleotide sequence of claim 1 into cells to inhibit IL-6 activity in the cells.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 356 base pairs
       (B) TYPE: nucleic acid (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 1:

CCCAGGATCC TTCTGGGAAT TCTGATCCTT CTGGGAATTC TGATCCTTCT GGGAATTCTG      60

ATCCTTCTGG GAATTCTGAT CCTTCTGGGA ATTCTGATCC TTCTGGGAAT TCTGATCCTT     120

CTGGGAATTC TGATCCTTCT GGGAATTCTG ATCTGCATCT CAATTAGTCA GCAACCATAG     180

TCCCGCCCCT AACTCCGCCC ATCCCGCCCC TAACTCCGCC CAGTTCCGCC CATTCTCCGC     240

CCCATGGCTG ACTAATTTTT TTTATTTATG CAGAGGCCGA GGCCGCCTCG GCCTCTGAGC     300

TATTCCAGAA GTAGTGAGGA GGCTTTTTTG GAGGCCTAGG CTTTTGCAAA AAGCTT        356

(2) INFORMATION FOR SEQ ID NO: 2:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 2:

GGATCCTTCT GGGAATTCTG ATCCTTCTGG GAATTCTG                              38

(2) INFORMATION FOR SEQ ID NO: 3:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 3:

CGCGGCCGCC TCGAGG                                                      16

(2) INFORMATION FOR SEQ ID NO: 4:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 4:

GATCCCTCGA GGCGGCCGCG GTAC                                             24

(2) INFORMATION FOR SEQ ID NO: 5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear     (ii) MOLECULE TYPE: cDNA    (iii) HYPOTHETICAL: NO     (iv) ANTI-SENSE: NO     (xi) SEQUENCE DESCRIPTION: SEQ ID NO: 5:

CTACGCGTGC AGTATTGACC CTTCCTCCT                      29

(2) INFORMATION FOR SEQ ID NO: 6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear     (ii) MOLECULE TYPE: cDNA    (iii) HYPOTHETICAL: NO     (iv) ANTI-SENSE: NO     (xi) SEQUENCE DESCRIPTION: SEQ ID NO: 6:

CGCAGATCTA GCTCACTTCT CCCCCTTC                       28